United States Patent
Beuckmann et al.

(10) Patent No.: US 11,096,941 B2
(45) Date of Patent: Aug. 24, 2021

(54) METHODS OF TREATING CIRCADIAN RHYTHM SLEEP DISORDERS

(71) Applicant: Eisai R&D Management Co., Ltd., Tokyo (JP)

(72) Inventors: Carsten T. Beuckmann, Ibaraki (JP); Margaret Moline, White Plains, NY (US); Andrew Satlin, Short Hills, NJ (US)

(73) Assignee: EISAI R&D MANAGEMENT CO.. LTD., Tokyo (JP)

( * ) Notice: Subject to any disclaimer, the term of this patent is extended or adjusted under 35 U.S.C. 154(b) by 148 days.

(21) Appl. No.: 16/300,335

(22) PCT Filed: May 11, 2017

(86) PCT No.: PCT/US2017/032228
§ 371 (c)(1),
(2) Date: Nov. 9, 2018

(87) PCT Pub. No.: WO2017/197160
PCT Pub. Date: Nov. 16, 2017

(65) Prior Publication Data
US 2020/0179382 A1 Jun. 11, 2020

Related U.S. Application Data

(60) Provisional application No. 62/335,599, filed on May 12, 2016, provisional application No. 62/335,611, filed on May 12, 2016, provisional application No. 62/413,976, filed on Oct. 27, 2016, provisional application No. 62/414,599, filed on Oct. 28, 2016, provisional application No. 62/414,606, filed on Oct. 28, 2016.

(51) Int. Cl.
*A61K 31/506* (2006.01)
*A61P 25/20* (2006.01)
*A61P 25/28* (2006.01)

(52) U.S. Cl.
CPC ............ *A61K 31/506* (2013.01); *A61P 25/20* (2018.01); *A61P 25/28* (2018.01)

(58) Field of Classification Search
CPC ......... A61K 31/506; A61P 25/20; A61P 25/28
See application file for complete search history.

(56) References Cited

U.S. PATENT DOCUMENTS

2011/0081385 A1 4/2011 Cremisi

FOREIGN PATENT DOCUMENTS

WO WO 2016/063995 A1 4/2016

OTHER PUBLICATIONS

Boss, C. et al: "Recent trends in orexin research—2010 to 2015" *Bioorganic & Medicinal Chemistry Letters*, vol. 25 No. 15, May 15, 2015 pp. 2875-2887.
Chow, M. et al., The hypocretin/orexin system in sleep disorders: preclinical insights and clinical progress. *Nature and Science of Sleep*, Mar. 14, 2016, vol. 2016, No. 8, pp. 81-86.
NCT03001557, Study of Lemborexant for Irregular Sleep-Wake Rhythm Disorder and Mild to Moderate Alzheimer's Disease Dementia. Dec. 23, 2016.
Roh, J. H. et al., Potential role of orexin and sleep modulation in the pathogenesis of Alzheimer's disease. *J. Exp. Med.*, Dec. 15, 2014, vol. 211, No. 13, pp. 2487-2496.
Satlin, A. et al., T70. Dual Orexin Receptor Antagonist E2006 Shows Efficacy on Sleep Initiation and Maintenance in Phase 2 Study. *Neuropsychopharmacology*, Dec. 9, 2014, vol. 39, No. Suppl. 1, pp. S336-S337.
Yoshida, Y. et al., Discovery of (1R,2S)-2-{[(2,4-Dimethylpyrimidin-5-yl)oxy]methyl}-2-(3-fluorophenyl)-N-(5-fluoropyridin-2-yl)clopropanecarboxamide (E2006): A Potent and Efficacious Oral Orexin Receptor Antagonist. *Journal of Medicinal Chemistry*, May 8, 2015, vol. 58, No. 11, pp. 4648-4664.
International Search Report for International Application No. PCT/US2017/032228 (6 pages).
Search Report for Singaporean Application No. 11201809527U Page from Intellectual Property Office of Singapore (date of search: Mar. 27, 2020) (3 pages).
Search Report for Russian Application No. 2018143809 (3 pages) and translation (3 pages).
Kelmanson I.A. "Sleep disorders in mentally retarded children," Current Pediatrics, 2014, 13(6). (3 pages)(translation: 9 pages).
Kolykhalov, I.V. "Behavioral and psychopathological symptoms in Alzheimer's disease: epidemiological, psychopathological and neurobiological aspects," Psychiatry, 2015, No. 3. (3 pages) (translation: 7 pages).
Preobrazhenskaya, I.S. "Cognitive Impairments and Sleep Disorders," 2015, No. 23. (3 pages) (translation: 8 pages).
Shunina, N. V. "The Influence of varying severity degrees of the brain injury on disorder of a night's sleep structure," 2013, No. 11. (2 pages) (translation: 4 pages).
Tang, Li-Na, et al. "Orexin and sleep-wake regulation," J. Int Pharm Res., vol. 42, No. 1, Feb. 2015, pp. 85-90.

*Primary Examiner* — Savitha M Rao
*Assistant Examiner* — Gregg Polansky
(74) *Attorney, Agent, or Firm* — Finnegan, Henderson, Farabow, Garrett & Dunner, LLP (57) ABSTRACT

Methods of treating irregular sleep-wake rhythm disorder in subjects and compositions for use in the same are disclosed.

19 Claims, 4 Drawing Sheets

FIG. 1A

Data represent least square means and standard errors
*: significant difference compared to R1 vehicle cohort (P<0.05, linear mixed model with Kenward-Roger)
†: significant difference compared to P8 vehicle cohort (P<0.05, linear mixed model with Kenward-Roger)

Data represent least square means and standard errors
*: significant difference compared to R1 vehicle cohort (P<0.05, linear mixed model with Kenward-Roger)
†: significant difference compared to P8 vehicle cohort (P<0.05, linear mixed model with Kenward-Roger)

FIG. 2

Data represent least square means and standard errors
*: significant difference compared to R1 vehicle cohort (P<0.05, linear mixed model with Kenward-Roger)
†: significant difference compared to P8 vehicle cohort (P<0.05, linear mixed model with Kenward-Roger)

METHODS OF TREATING CIRCADIAN RHYTHM SLEEP DISORDERS

The present application is a national stage application under 35 U.S.C. § 371 of International Application No. PCT/US2017/032228, filed May 11, 2017, which designated the U.S. and which claims the benefit of priority to U.S. Provisional Application No. 62/335,599 filed May 12, 2016, U.S. Provisional Application No. 62/335,611 filed May 12, 2016, U.S. Provisional Application No. 62/413,976 filed Oct. 27, 2016, U.S. Provisional Application No. 62/414,599 filed Oct. 28, 2016, and U.S. Provisional Application No. 62/414,606 filed Oct. 28, 2016; the entire contents of each are incorporated herein by reference.

Novel methods for and compositions for use in treating at least one circadian rhythm sleep disorder using a compound of Formula (I), or pharmaceutically acceptable salts and solvates thereof, are disclosed.

Irregular Sleep-Wake Rhythm Disorder ("ISWRD") is an internationally recognized and accepted disorder. The sleep-wake pattern exhibited by subjects with ISWRD is diagnostically distinct from insomnia. Unlike insomnia disorder, subjects with ISWRD are sleeping intermittently and irregularly during the day in addition to not sleeping continuously at night. In contrast, subjects with insomnia may have reduced sleep maintenance, but are not sleeping intermittently and irregularly during the day. ISWRD disturbances are therefore sometimes referred to as fragmentation of the normal circadian, or 24-hour, diurnal pattern of sleep and wake.

ISWRD is identified and coded as a distinct disorder in several International Classification systems including Circadian Rhythm Sleep Disorder, Irregular Sleep-Wake Type G47.23 (ICD-10); Circadian Rhythm Sleep Disorder, Irregular Sleep-Wake Type 307.45-3 (DSM-5); and Circadian Rhythm Sleep-Wake Disorder, Irregular Sleep-Wake Rhythm Disorder 307.45-3 (ICSD-3).

There exists an unmet medical need for a safe and effective therapy that is conveniently administered to address the irregular sleep and wake pattern, which in turn could help with problematic behaviors (e.g., sundowning, restlessness, agitation, and/or wandering) and cognitive difficulties (e.g., with memory and/or attention) associated with ISWRD.

The orexin neurotransmitter pathway is directly involved in modulation of the circadian sleep-wake rhythm, with orexins promoting wakefulness. Orexin receptors are G-protein coupled receptors found predominately in the brain. Their endogenous ligands, orexin-A and orexin-B, are expressed by neurons localized in the hypothalamus. Orexin-A is a 33 amino acid peptide and orexin-B is a 28 amino acid peptide. Sakurai, T., et al., Cell, 1998, 92, 573-85. There are two subtypes of orexin receptors: orexin receptor 1 and orexin receptor 2. Orexin receptor 1 binds orexin-A preferentially, while orexin receptor 2 binds both orexin-A and orexin-B. It has been observed that orexins control wake-sleep conditions. Chemelli, R. M., et al., Cell, 1999, 98, 437-51. Lemborexant is being studied for the treatment of insomnia disorder and for the treatment of at least one circadian rhythm sleep disorder in subjects suffering from dementia due to Alzheimer's disease ("AD") and/or related disorders and/or mild cognitive impairment due to Alzheimer's disease. See, e.g., U.S. Patent Application Publication No. 2012/0095031 and U.S. Provisional Patent Application Nos. 62/335,599 and 62/335,611, the contents of which are herein incorporated by reference.

In some embodiments, a method of treating at least one circadian rhythm sleep disorder comprising administering to a subject in need thereof an effective amount of a compound of Formula (I), or pharmaceutically acceptable salts and solvates thereof, is provided. In some embodiments, the at least one circadian rhythm sleep disorder may be chosen from sleep disruption, sleep-wake fragmentation, circadian rhythm sleep disorder, and ISWRD. In some embodiments, the at least one circadian rhythm sleep disorder is ISWRD. In some embodiments, the ISWRD is due to traumatic brain injury. In some embodiments, the ISWRD is due to neurodevelopmental disorders.

In some embodiments, ISWRD is due to dementia. In some embodiments, ISWRD is due to dementia due to Alzheimer's disease and/or related disorders. In some embodiments, ISWRD is due to mild cognitive impairment due to Alzheimer's disease. In some embodiments, ISWRD is due to mild cognitive impairment due to related disorders. In some embodiments, the ISWRD is due to dementia due to related disorders. In some embodiments, the dementia due to related disorders is chosen from vascular dementia, fronto-temporal dementia, Parkinson's Disease, and dementias due to other causes. In some embodiments, the dementia due to related disorders is Parkinson's Disease. In some embodiments, the subject suffers from at least one other circadian rhythm sleep disorder in addition to ISWRD.

AD and related disorders are a large and increasing public health concern, as the population of older adults increases globally. Among the many symptoms that are associated with dementia, sleep and wake disturbances are both common and are risk factors themselves that contribute to the development and worsening of the neuropathology and symptomatology, including cognitive function and behavioral disturbances commonly referred to in the aggregate as Behavioral and Psychological Symptoms of Dementia (BPSD), based on animal models and human studies.

Sleep and wake disturbances appear early in the course of disease, e.g., Alzheimer's Disease, dementia, etc., and are associated generally with a loss of circadian rhythmicity. Dementia subjects have a marked decrease in sleep maintenance when they attempt to sleep during the night and spend a large portion of the day asleep. This pattern is referred to as sleep-wake fragmentation and is characterized by decreased amplitudes of the sleep-wake and alertness rhythms, with less predictability of the sleep-wake pattern from day to day.

As dementia progresses, subjects often exhibit behavioral disturbances such as agitation and night wandering. They often manifest disturbed behaviors that are often described as "sundowning" because of their occurrence in the late afternoon and early evening. Disrupted sleep can also increase the risk for falling, based in part on disorientation after awakening from sleep. It has been shown that subjects with the most disturbed sleep at night have more problematic behaviors during the day, for example, restlessness, agitation, and wandering. These behaviors, which also disrupt the sleep of caregivers, are reasons underlying some decisions to institutionalize dementia subjects.

Animal and human studies support the view that poor sleep is associated with amyloid burden in AD. Recent studies have shown that levels of amyloid beta ("Aβ", a type of peptide that can aggregate into toxic forms) in the brain correlate with time spent awake, subsequently decreasing during sleep. Sleep deprivation increases the concentration of soluble Aβ and results in chronic accumulation of Aβ, whereas sleep extension has the opposite effect. Kang, J.-E., et al., Science, 2009, 326, 1005-7. Roh, J. H., et al., J. Exp.

Med., 2014, 211, 2487-96. Disrupted sleep has been associated with higher Aβ levels and impaired learning. Mander, B. A., et al., Nat. Neurosci., 2015, 18, 1051-7. Once Aβ accumulates and toxic aggregates and insoluble fibrils that lead to amyloid plaque develop, these may impair brain function and/or lead to neuronal degeneration that leads to increased wakefulness and altered sleep patterns.

Taken together, these studies highlight the bi-directionality of the problem. The neuropathological changes associated with dementia worsen sleep, and poor sleep worsens cognitive function and may contribute directly to the progression of the pathological disease process and the clinical course of illness. If sleep has a normalizing/reducing function on Aβ levels, helping AD subjects to restore normal sleep patterns might result in reduced Aβ depositions.

Thus, there exists an unmet medical need for a safe and effective therapy that is conveniently administered to address sleep-wake fragmentation in patients with ISWRD, which in turn would help with the problematic behaviors (e.g., sundowning, restlessness, agitation, and/or wandering) and cognitive difficulties (e.g., with memory and/or attention) associated with dementia due to Alzheimer's disease and/or related disorders, and/or mild cognitive impairment due to Alzheimer's disease, and may also help to slow the brain degeneration that occurs in AD by reducing the accumulation of Aβ. Increased sleep duration, especially with particular sleep stages such as slow-wave sleep and REM sleep, may improve cognition. These stages are associated with performance on working memory tasks and memory consolidation, respectively. Targeting sleep may also improve behavioral disturbances in AD.

In animal models of Alzheimer's disease, orexin was found to increase soluble Aβ accumulation in the brain; conversely, chronic treatment with a dual orexin receptor antagonist or knocking out the orexin gene decreased soluble Aβ and Aβ plaque accumulation. Kang, J.-E., et al., Science, 2009, 326, 1005-7; Roh, J. H., et al., Journal of Experimental Medicine, 2014, 211, 2487-96. Accumulation of Aβ plaque is associated with dementias such as AD. In some embodiments, there is a reduction in the accumulation of Aβ plaque in the brain. In some embodiments, there is a reduction of soluble toxic Aβ aggregates.

In some embodiments, a method of improving continuity of nocturnal sleep in a subject with ISWRD comprising administering an effective amount of a compound of Formula (I), or pharmaceutically acceptable salts and solvates thereof, to a subject in need thereof is provided.

In some embodiments, a method of improving behaviors and cognitive difficulties associated with ISWRD in a subject comprising administering an effective amount of a compound of Formula (I), or pharmaceutically acceptable salts and solvates thereof, to a subject in need thereof is provided.

In some embodiments, a method of treating or alleviating ISWRD in a subject comprising administering an effective amount of a compound of Formula (I), or pharmaceutically acceptable salts and solvates thereof, to a subject in need thereof is provided. In some embodiments, the ISWRD may be associated with dementias such as AD.

In some embodiments, a method for treating excessive daytime sleepiness and/or voluntary or involuntary napping in a subject with ISWRD comprising administering an effective amount of a compound of Formula (I), or pharmaceutically acceptable salts and solvates thereof, to a subject in need thereof is provided.

In some embodiments, the at least one circadian rhythm sleep disorder is chosen from sleep disruption, sleep fragmentation, circadian rhythm sleep disorder, and irregular sleep-wake rhythm disorder.

In some embodiments, a method of stabilizing one or more circadian rhythms in a subject comprising administering an effective amount of a compound of Formula (I), or pharmaceutically acceptable salts and solvates thereof, to a subject in need thereof is provided. In some embodiments, a method of improving one or more circadian rhythms in a subject comprising administering an effective amount of a compound of Formula (I), or pharmaceutically acceptable salts and solvates thereof, to a subject in need thereof is provided.

In some embodiments, a method of improving continuity of nocturnal sleep in a subject with dementia comprising administering an effective amount of a compound of Formula (I), or pharmaceutically acceptable salts and solvates thereof, to a subject in need thereof is provided. In some embodiments, the dementia is due to Alzheimer's disease and/or related disorders. In some embodiments, a method of improving continuity of nocturnal sleep in a subject with mild cognitive impairment due to Alzheimer's disease comprising administering an effective amount of a compound of Formula (I), or pharmaceutically acceptable salts and solvates thereof, to a subject in need thereof is provided.

In some embodiments, a method of improving behaviors and cognitive difficulties associated with dementia in a subject with dementia comprising administering an effective amount of a compound of Formula (I), or pharmaceutically acceptable salts and solvates thereof, to a subject in need thereof is provided. In some embodiments, the dementia is due to Alzheimer's disease and/or related disorders.

In some embodiments, a method for treating excessive daytime sleepiness and/or napping in a subject with dementia comprising administering an effective amount of a compound of Formula (I), or pharmaceutically acceptable salts and solvates thereof, to a subject in need thereof is provided. In some embodiments, the dementia is due to Alzheimer's disease and/or related disorders. In some embodiments, a method for treating excessive daytime sleepiness and/or napping in a subject with mild cognitive impairment due to Alzheimer's disease comprising administering an effective amount of a compound of Formula (I), or pharmaceutically acceptable salts and solvates thereof, to a subject in need thereof is provided.

In some embodiments, the methods described herein may consolidate sleep during the nighttime hours. In some embodiments, the methods described herein may consolidate wakefulness during the daytime hours. In some embodiments, there may be an increase in wake efficiency. In some embodiments, there may be an increase in sleep efficiency. In some embodiments, the methods described herein may decrease daytime sleepiness. In some embodiments, there may be a decrease in daytime sleepiness and/or daytime napping. In some embodiments, daytime alertness may be improved. In some embodiments, a stabilization of one or more circadian rhythms may result. In some embodiments, an improvement of one or more circadian rhythms may result.

In some embodiments, there is a clinical stabilization in cognitive impairment due to Alzheimer's disease in the subject. In some embodiments, there is a clinical improvement in cognitive impairment due to Alzheimer's disease in the subject. In some embodiments, there is a clinical reduction in rate of decline in cognitive impairment due to Alzheimer's disease in the subject. In some embodiments, there is a clinical stabilization in the subject with dementia due to Alzheimer's disease and/or related disorders. In some embodiments, there is a clinical improvement in the subject with dementia due to Alzheimer's disease and/or related disorders. In some embodiments, there is a clinical reduction in rate of decline in the subject with dementia due to Alzheimer's disease and/or related disorders. In some embodiments, the methods described herein decrease behavioral disturbances in the subject.

As used herein, the following definitions shall apply unless otherwise indicated.

As used herein, the term "compound of Formula (I)" refers to lemborexant, a compound having the structure:

, also known as (1R,2S)-2-(((2,4-dimethylpyrimidin-5-yl)oxy)methyl)-2-(3-fluorophenyl)-N-(5-fluoropyridin-2-yl)cyclopropanecarboxamide or (1R,2S)-2-(((2,4-dimethylpyrimidin-5-yl)oxy)methyl)-2-(3-fluorophenyl)-N-(5-fluoropyridin-2-yl)cyclopropane-1-carboxamide, or pharmaceutically acceptable salts and solvates thereof. In some embodiments, the compound of Formula (I) may be a free base, a pharmaceutically acceptable salt, a hydrate or other solvate, a polymorph, or a combination of any two or more of the foregoing. In some embodiments, the compound of Formula (I) may be a free base. In some embodiments, the compound of Formula (I) may be a pharmaceutically acceptable salt of a compound of Formula (I). In some embodiments, the compound of Formula (I) may be a solvate of a compound of a compound of Formula (I). In some embodiments, the compound of Formula (I) may be a hydrate of a compound of Formula (I). In some embodiments, the compound of Formula (I) may be a polymorph of a compound of Formula (I).

As used herein, the term "effective amount" means an amount sufficient to effect an intended result including, but not limited to, treatment of at least one symptom associated with a disorder or condition, such as, for example, ISWRD and/or Alzheimer's disease, as illustrated below.

As used herein, the term "subject" means an animal subject, such as a mammalian subject, and for example, a human being. As used herein, the subject may be of any age. In some embodiments, the age of the subject may range from less than one year to more than 95 years of age. In some embodiments, the age of the subject may range from less than one year to 15 years of age. In some embodiments, the age of the subject may range from 10 years of age to 30 years of age. In some embodiments, the age of the subject may range from 25 years of age to 45 years of age. In some embodiments, the age of the subject may range from 40 years of age to 60 years of age. In some embodiments, the age of the subject may range from 55 years of age to 75 years of age. In some embodiments, the age of the subject may range from 70 years of age to 95 years of age. In some embodiments, the age of the subject may range from 60 years of age to 95 years of age.

As used herein, the terms "treatment" and "treating" refer to an approach for obtaining beneficial or desired results including, but not limited to, therapeutic benefit and/or prophylactic benefit.

As used herein, the term "ISWRD", also known as "irregular sleep-wake pattern disorder" and "irregular sleep-wake rhythm disorder", means a sleep cycle that is characterized in potentially having a sleep-wake pattern, however it may be accompanied by a rhythm wherein the amplitude of this rhythm may be reduced, or the phase of the pattern may be delayed or advanced, or the period of the pattern may be shortened or lengthened, or fragmentation of the pattern may occur.

With ISWRD, a major sleep period is less well articulated, and in some embodiments, sleep is fragmented into, for example, at least three or four periods during a 24-hour day. In some embodiments, the sleep is fragmented into, for example, at least three periods during a 24-hour day. In some embodiments, the sleep is fragmented into, for example, at least four periods during a 24-hour day. The number of sleep fragmentations may vary from day to day. See, e.g., Diagnostic and Statistical Manual of Mental Disorders, Fifth Edition, 2013, 394-95. This disorder is one of the circadian rhythm sleep disorders, and is different from general insomnia disorder. In some embodiments, ISWRD may be due to traumatic brain injury. See, e.g., Viola-Saltzman, M. and Watson, N. F., Neurol. Clin., 2012, 30, 1299-1312 (describing a potential link between traumatic brain injury and irregular sleep-wake rhythm disorder). In some embodiments, ISWRD may be due to at least one neurodevelopmental disorder. See, e.g., Abbott, S. M. and Zee, P. C., Sleep Med. Clin., 2015, 10, 517-22. In some embodiments, the at least one neurodevelopmental disorder may be selected from Angelman Syndrome, autism, mental retardation, and Down Syndrome. See id. In some embodiments, the at least one neurodevelopmental disorder may be Angelman Syndrome. In some embodiments, the at least one neurodevelopmental disorder may be autism. In some embodiments, the at least one neurodevelopmental disorder may be mental retardation. In some embodiments, the at least one neurodevelopmental disorder may be Down Syndrome. In some embodiments, ISWRD may be due to dementia. In some embodiments, ISWRD may be due to Parkinson's Disease. In some embodiments, ISWRD may be due to dementia due to Alzheimer's Disease. See, e.g., Vitiello, M. V. and Zee, P. C., Sleep Med. Clin., 2009, 4, 213-18. In some embodiments, ISWRD may be due to dementia due to related disorders. See, e.g., id. In some embodiments, ISWRD may be due to dementia due to mild cognitive impairment, e.g., traumatic brain injury. See, e.g., id.

According to the DSM-V, Circadian Rhythm Sleep-Wake Disorders of the Irregular Sleep-Wake Type, are described as "[a] temporally disorganized sleep-wake pattern, such that the timing of sleep and wake periods is available through the 24-hour period." See, e.g., Diagnostic and Statistical Manual of Mental Disorders, Fifth Edition, 2013, 390.

As used herein, the term "at least one circadian rhythm sleep disorder" means at least one condition chosen from sleep disruption, sleep-wake fragmentation, circadian rhythm sleep disorder, and ISWRD.

As used herein, the term "at least one other circadian rhythm sleep disorder" means that a subject suffers from ISWRD and at least one other condition chosen from sleep disruption and circadian rhythm sleep disorder.

As used herein, the term "sleep disruption," also known as "interrupted sleep," "divided sleep," "fragmented sleep," and "segmented sleep," among other terms, means a sleep pattern where nighttime sleep is punctuated by one or more periods of wakefulness and daytime is punctuated by one or more periods of sleep. Sleep disruption may be assessed by, for example, wake time after sleep onset (WASO), sleep efficiency, duration of awakenings, and/or number of awakenings (NAW) and sleep fragmentation index (SFI).

As used herein, the term "wake disruption" means a wake pattern where daytime wakefulness is punctuated by two or more periods of sleep.

As used herein, the term "wake efficiency" refers to the amount of time awake/time out of bed, and includes the number and duration or planned and spontaneous sleep bouts.

As used herein, the term "sleep-wake fragmentation", also known as "fragmented sleep and wake", is a disorder characterized by a nocturnal sleep period punctuated by one or more periods of wakefulness and which may be shorter in duration than the subject slept prior to the onset of any of the causes of the sleep disorders. The time spent sleeping during the nighttime sleep period, at any sleep stage, is less continuous than normal.

As used herein, the term "circadian rhythm sleep disorders" is a family of disorders that affect, among other bodily processes, the timing of sleep. A circadian rhythm sleep disorder may be characterized by at least one disruption or disturbance chosen from the following:
   A. A persistent or recurrent pattern of sleep disruption that is primarily due to an alteration of the circadian system or to a misalignment between the endogenous circadian rhythm and the sleep-wake schedule required by an individual's physical environment or social or professional schedule;
   B. The sleep disruption leads to an excessive sleepiness or insomnia, or both; and
   C. The sleep disturbance causes clinically significant distress or impairment in social, occupational, and other important areas of functioning.
See e.g., id. at 390-98.

As used herein, the terms "stabilization of one or more circadian rhythms," "stabilizing one or more circadian rhythms," and "stabilizing a circadian rhythm" mean no increase in one or more disturbances and/or disruptions associated with a circadian rhythm sleep disorder.

As used herein, the terms "improving one or more circadian rhythms," "improvement of one or more circadian rhythms," and "improvement of a circadian rhythm" means a reduction in one or more disturbances and/or disruptions associated with a circadian rhythm sleep disorder.

As used herein, the term "dementia" refers to a neurocognitive disorder. See, e.g., Diagnostic and Statistical Manual of Mental Disorders, Fifth Edition, 2013, 602-14; Albert, M. S. et al., Alzheimer's & Dementia, 2011, 7, 271-72; McKhann, G. M., et al., Alzheimer's & Dementia, 2011, 7, 265; Dubois, B., et al., Lancet Neurol., 2014, 13, 614-29.

As used herein, the term "dementia due to Alzheimer's Disease" includes an insidious onset and gradual progression of behavioral symptoms including, but not limited to, cognitive difficulties, including memory loss and diminished thinking skills. See, e.g., Diagnostic and Statistical Manual of Mental Disorders, Fifth Edition, 2013, 602-14; Albert, M. S. et al., Alzheimer's & Dementia, 2011, 7, 271-72; McKhann, G. M., et al., Alzheimer's & Dementia, 2011, 7, 265; Dubois, B., et al., Lancet Neurol. 2014, 13, 614-29.

As used herein, the term "dementia due to related disorders" includes an insidious onset and gradual progression of behavioral symptoms including, but not limited to, cognitive difficulties, including memory loss and diminished thinking skills. The related disorders include, for example, vascular dementia, fronto-temporal dementia, Parkinson's Disease, and dementias due to other causes (e.g., traumatic brain injury, infection with human immunodeficiency virus (HIV), etc.).

As used herein, the term "mild cognitive impairment due to related disorders" means a slight but noticeable and measurable decline in cognitive abilities, e.g., memory and thinking skills, due to disorders such as, for example, vascular dementia, fronto-temporal dementia, Parkinson's Disease, and dementias due to other causes (e.g., infection with human immunodeficiency virus (HIV)).

As used herein, the term "mild cognitive impairment due to Alzheimer's disease" means a slight but noticeable and measurable decline in cognitive abilities, e.g., memory and thinking skills, due to Alzheimer's disease, and is discussed in, e.g., Diagnostic and Statistical Manual of Mental Disorders, Fifth Edition, 2013, 602-14; Albert, M. S. et al., Alzheimer's & Dementia, 2011, 7, 271-72; McKhann, G. M., et al., Alzheimer's & Dementia, 2011, 7, 265; Dubois, B., et al., Lancet Neurol., 2014, 13, 614-29.

As used herein, the terms "clinical stabilization in mild cognitive impairment due to Alzheimer's disease" and "clinical stabilization in dementia due to Alzheimer's disease and/or related disorders" mean stabilization or no or insignificant decline in at least one domain chosen from cognitive, functional, and behavioral, including but not limited to mood, activities of daily living, agitation, restlessness, etc.

As used herein, the terms "clinical improvement in mild cognitive impairment due to Alzheimer's disease" and "clinical improvement in dementia due to Alzheimer's disease and/or related disorders" mean improvement in at least one domain chosen from cognitive, functional, and behavioral, including but not limited to mood, activities of daily living, agitation, restlessness, etc.

As used herein, the terms "clinical reduction in rate of decline in mild cognitive impairment due to Alzheimer's disease" and "clinical reduction in rate of decline in dementia due to Alzheimer's disease and/or related disorders" mean a decrease in the rate of decline in at least one domain chosen from cognitive, functional, and behavioral, including but not limited to mood, activities of daily living, agitation, restlessness, etc.

As used herein, the term "clinical stabilization in ISWRD" means stabilization or no or insignificant decline in at least one domain chosen from sleep-wake fragmentation, amplitudes of the sleep-wake and alertness rhythms, the sleep-wake pattern from day to day, sleep efficiency, wake efficiency, etc.

As used herein, the term "clinical improvement in ISWRD" means improvement in at least one domain chosen from sleep-wake fragmentation, amplitudes of the sleep-wake and alertness rhythms, the sleep-wake pattern from day to day, sleep efficiency, wake efficiency, etc.

As used herein, the term "clinical reduction in rate of decline in ISWRD" means a decrease in the rate of decline in at least one domain chosen from at least one domain of sleep-wake fragmentation, amplitudes of the sleep-wake and alertness rhythms, the sleep-wake pattern from day to day, sleep efficiency, wake efficiency, etc.

As used herein, the term "continuity of nocturnal sleep" means sleep that is continuous (i.e., few awakenings, with each lasting only a short time) and during the nighttime hours.

As used herein, the term "sleep time" refers to the time that a subject spends asleep. Sleep time may be continuous or discontinuous.

As used herein, the term "sleep efficiency" refers to the total sleep time a subject obtains during his or her time in bed. Sleep efficiency is measured by the equation: sleep efficiency=100%*(total sleep time/total time in bed).

As used herein, the term "behavioral and psychological symptoms of dementia", also known as, "BPSD", represents a heterogeneous group of non-cognitive symptoms and behaviors occurring in subjects with dementia. These symptoms are as clinically relevant as cognitive symptoms as they strongly correlate with the degree of functional and cognitive impairment. Symptoms include, for example, agitation, aberrant motor behavior, anxiety, elation, irritability, depression, apathy, disinhibition, delusions, hallucinations, and sleep or appetite changes. See, e.g., Mukaetova-Ladinska, E. B., et al., Front. Neurol., 2012, 3, Art. 73.

As used herein, a "decrease in daytime sleepiness" means an increase and/or stabilization in the percentage of time spent awake during the daytime.

As used herein, a "decrease in daytime napping" means a decrease in the number and duration of daytime napping (planned and unplanned).

As used herein, an "improvement in daytime alertness" means stabilization, improvement, and/or slower rate of decline in assessments of alertness.

As used herein, a "decrease in behavioral disturbances" means stabilization, improvement, and/or slower rate of decline in assessments of agitation and/or behavioral disturbance.

Subjective and objective determinations, for example, actigraphy, of the aforementioned circadian rhythm sleep disorders and quality are known in the art. In some embodiments, the at least one circadian rhythm sleep disorder is determined by subjective measurements, such as, for example, asking the subject, maintaining a sleep diary, or assessment via a standardized questionnaire regarding how restorative and undisturbed sleep has been (e.g., Pittsburgh Sleep Quality Index (Buysse et al., Psychiatry Research, 1989, 28, 193-213)). In some embodiments, the at least one circadian rhythm sleep disorder is determined by observing the subject, such as, for example, observing how long it takes the subject to fall asleep, how many times the subject wakes up during the night, how agitated the subject is (e.g., physical or verbal agitation), how aggressive the subject's behavior is, how disoriented the subject is upon awakening, etc. In some embodiments, the at least one circadian rhythm sleep disorder is determined using polysomnography. Polysomnography is the monitoring of multiple electrophysiological parameters during sleep and generally includes measurement of EEG activity, electro-oculographic activity and electromyographic activity, as well as other measurements. These results, along with observations, can measure not only sleep latency (the amount of time required to fall asleep), but also sleep continuity (overall balance of sleep and wakefulness, or the percentage of time spent asleep or the amount of time spent awake after sleep onset) which may be an indication of the quality of sleep. Actigraphic measurement techniques may be used as well. Actigraphy is the objective measurement of motor activity in a subject using a device that is worn on the body, generally the non-dominant wrist.

As used herein, the term "excipient" shall mean an inactive ingredient used as a vehicle (e.g., water, capsule shell, etc.), a diluent, or a component to constitute a dosage form or pharmaceutical composition comprising a drug such as a therapeutic agent. The term also encompasses an inactive ingredient that imparts cohesive function (e.g., binder), disintegrating function (e.g., disintegrator), lubricant function (e.g., lubricating agent), and/or the other function (e.g., solvent, surfactant, etc.) to the composition.

As used herein, the term "pharmaceutically acceptable carrier" refers to a nontoxic carrier, adjuvant, and/or vehicle that does not destroy the pharmacological activity of the compound with which it is formulated. Pharmaceutically acceptable carriers, adjuvants and/or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol, and wool fat.

As used herein, the term "pharmaceutically acceptable salt" is a salt that retains the desired biological activity of the parent compound and does not impart undesired toxicological effects. Examples of such salts include, but are not limited to: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes, et al., J. Pharm. Sci., 2005, 94, 10; and Berge, et al., J. Pharm. Sci., 1977, 66, 1, which are incorporated herein by reference.

Dosage forms of the present disclosure contain compound of Formula (I), or pharmaceutically acceptable salts and solvates thereof, in a therapeutically effective amount for treatment of, e.g., ISWRD when administered in accordance with the teachings of the present disclosure. Unit dose of the effective amount in a dosage form is from 0.5 mg to 100 mg, from 2 mg to 75 mg, from 2 mg to 70 mg, from 2 mg to 65 mg, from 2 mg to 60 mg, from 2 mg to 55 mg, from 2 mg to 50 mg, from 2 mg to 45 mg, from 2 mg to 40 mg, from 2 mg to 35 mg, from 2 mg to 30 mg, from 2 mg to 25 mg, from 2 mg to 20 mg, from 1 mg to 15 mg, from 2 mg to 15 mg, or chosen from 2 mg, 2.5 mg, 4 mg, 5 mg, 8 mg, 10 mg, or 15 mg. Unit dose is not limited by the type of the dosage form or the number of dosage forms for single dose. In some embodiments, the unit dose may be 2.5 mg. In some embodiments, the unit dose may be 5 mg. In some embodiments, the unit dose may be 10 mg. In some embodiments, the unit dose may be 15 mg.

In some embodiments, a dosage form of the present disclosure may constitute one or more pharmaceutical compositions comprising the compound of Formula (I), or pharmaceutically acceptable salts and solvates thereof, together with pharmaceutically acceptable excipients.

As used herein, the term "composition" used herein includes a product comprising a particular ingredient in a particular amount and any product directly or indirectly brought about by the combination of particular ingredients in particular amounts. Such a term related to the pharmaceutical composition is intended to include a product comprising an active ingredient and an inert ingredient constituting a carrier and include every product directly or indirectly brought about by the combination, complexation or aggregation of any two or more ingredients or the dissociation, other kinds of reactions or interaction of one or more ingredients. Thus, the pharmaceutical composition of the present disclosure includes every composition prepared by mixing the compound of the present disclosure with a pharmaceutically acceptable carrier.

As used herein, the term "pharmaceutically acceptable" means that a carrier, diluent, excipient, or vehicle is compatible with other components of a formulation and is nontoxic to a subject.

Solid dosage forms of the present disclosure include capsules, granules, lozenges, pellets, pills, powders, suspensions, and tablets.

The pharmaceutical compositions of the present disclosure may be prepared using standard techniques and manufacturing processes generally known in the art. See, e.g., the monograph of *Japanese Pharmacopoeia*, 16$^{th}$ *Edition*; and *Pharmaceutical Dosage Forms of U.S. Pharmacopoeia-NF*, Chapter 1151.

In some embodiments, pharmaceutical compositions comprise a compound of Formula (I), or pharmaceutically acceptable salts and solvates thereof. In some embodiments, pharmaceutical compositions further comprise at least one additional component chosen from pharmaceutically acceptable carriers, pharmaceutically acceptable vehicles, and pharmaceutically acceptable excipients.

In some embodiments, the at least one additional component in the pharmaceutical compositions is chosen depending upon the route of administration for which the pharmaceutical composition is intended. Non-limiting examples of suitable routes of administration for which the pharmaceutical composition may be used include parenteral, oral, inhalation spray, topical, rectal, nasal, buccal, vaginal and implanted reservoir administration. The term "parenteral" as used herein includes subcutaneous, intravenous, intramuscular, intra-articular, intra-synovial, intrasternal, intracisternal, intrathecal, intrahepatic, intralesional and intracranial injection or infusion techniques. In some embodiments, the mode of administration is chosen from intravenous, oral, subcutaneous, and intramuscular administration. Sterile injectable forms of the compositions of this disclosure may be, for example, aqueous or oleaginous suspension. These suspensions may be formulated according to techniques known in the art using suitable dispersing or wetting agents and suspending agents known in the art. The sterile injectable preparation may also be a sterile injectable solution or suspension in a nontoxic parenterally acceptable diluent or solvent, for example, as a solution in 1,3-butanediol. Non-limiting examples of vehicles and solvents that may be employed include water, Ringer's solution, and isotonic sodium chloride solution. In addition, sterile, fixed oils may be employed as a solvent and/or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, and/or other dosage forms, may also be used for the purposes of formulation.

For oral administration, the compound of Formula (I), or pharmaceutically acceptable salts and solvates thereof, may be provided in an acceptable oral dosage form, including, but not limited to, capsules, tablets, oral disintegrating tablet, sprinkles, and other oral formulations that would be easy to swallow. In some embodiments, the compound of Formula (I), or pharmaceutically acceptable salts and solvates thereof, is provided in the form of tablet or capsules. In some embodiments, the compound of Formula (I), or pharmaceutically acceptable salts and solvates thereof, is provided in the form of crushable tablets. In the case of tablets for oral use, carriers commonly used include lactose and cornstarch. Lubricating agents, such as magnesium stearate, may also be added. For oral administration in a capsule form, useful diluents include lactose and dried cornstarch. When aqueous suspensions are required for oral use, the active ingredient is combined with an emulsifying and/or suspending agent. If desired, certain sweetening, flavoring or coloring agents may also be added.

In order that the disclosure described herein may be more fully understood, the following examples are set forth. It should be understood that these examples are for illustrative purposes only and are not to be construed as limiting this disclosure in any manner.

EXAMPLES

Example 1

TABLE 1

| Component | Tablet Strength | | |
|---|---|---|---|
| (all quantities stated in mg) | 2.5 mg | 5 mg | 10 mg |
| Core Tablet Internal Phase (added in granulation process) | | | |
| Compound of Formula (I) [a] | 2.5 | 5 | 10 |
| Lactose monohydrate [b] | 96.38 | 93.88 | 88.88 |
| Low-substituted hydroxypropyl cellulose | 10.8 | 10.8 | 10.8 |
| Hydroxypropyl cellulose | 3.6 | 3.6 | 3.6 |
| Purified water [c] | q.s. | q.s. | q.s. |

TABLE 1-continued

| Component | Tablet Strength | | |
|---|---|---|---|
| (all quantities stated in mg) | 2.5 mg | 5 mg | 10 mg |
| External Phase (added in blending process) | | | |
| Low-substituted hydroxypropyl cellulose [d] | 6 | 6 | 6 |
| Magnesium stearate [d] | 0.72 | 0.72 | 0.72 |
| Core Tablet Weight | 120 | 120 | 120 |
| Film-coat | | | |
| OPADRY 03F43101 Orange [e] | 7.2 | 7.2 | 7.2 |
| Purified water [c] | q.s. | q.s. | q.s. |
| Total Weight (mg) | 127.2 | 127.2 | 127.2 |

[a] Quantity of compound of Formula (I) is adjusted based on its purity (impurities, residual solvents, etc.).
[b] Quantity of lactose monohydrate for compounding is adjusted depending on the quantity of compound of Formula (I) in order to maintain constant weight of core tablets.
[c] Removed during drying process.
[d] Adjusted proportionally to the yield of sized granules.

Example 2. Effect of Administration of a Compound of Formula (I) on Sleep Cycles of Mice A compound of Formula (I) was finely crushed and suspended in vehicle, a mixture of 0.5% w/v methylcellulose 400 cP in distilled water. Experimental data were collected on male senescence accelerated mouse prone-8 ("SAMP8" or "P8") strain animals and male senescence accelerated mouse resistant-1 ("SAMR1" or "R1") strain animals at the age of 21 weeks. P8 mice are known to show accelerated symptoms of aging and also pathological and behavioral symptoms of Alzheimer's disease, while R1 mice are used to represent a normal aging process and are also used as a control strain for P8 mice. See, e.g., Miyamoto, et al., Exp. Geron., 1997, 32, 139-48; Morley et al., Curr. Pharm. Des., 2012, 18, 1123-30.

Electroencephalogram ("EEG") and electromyogram ("EMG") electrodes were implanted on each mouse at 17-18 weeks of age, and the mice were then allowed to recover for at least 18 days in individual recording cages, where they could freely move, under a 12-hour light/12-hour dark cycle. Amplified EEG and EMG signals were digitally recorded for 3 days, separated into individual 24-hour recordings, which were initiated at each lights-on event. During the first 30 minutes of the light cycle (ZT 0-0.5), each mouse received an oral administration of either vehicle or 3 mg/kg of the compound of Formula (I) in vehicle or 30 mg/kg of the compound of Formula (I) in vehicle, after which the sleep/wake behavior of mice was recorded until the next lights on event. Each mouse received every treatment in a cross-over fashion with one treatment per day in the following order: vehicle (10 mL/kg bodyweight), 3 mg/kg, and then 30 mg/kg. Some mice started with vehicle on day 1, some mice started with 3 mg/kg compound of Formula (I) on day 1, and some mice started with 30 mg/kg compound of Formula (I) on day 1.

EEG frequency and EMG activity signal data were analyzed using software from Kissei Comtec Co., Ltd. to characterize every 10 second epoch as either rapid eye movement (REM) sleep, non-REM sleep, or wakefulness. Then, accumulated wakefulness, non-REM sleep, and REM sleep times over the light cycle (11.5 hours) and the dark cycle (12 hours) were calculated. Additionally, latencies to sleep and REM sleep were calculated as the first appearance of 6 or more epochs of uninterrupted sleep or one or more epochs of REM sleep after the dosing event, respectively.

The circadian rhythm parameter phase was determined as the inflection point of a cosine curve fit to the wakefulness distribution in 30 minute bins across the day for every individual mouse using JTK_CYCLE software. Hughes, et al., J. Biol. Rhythms, 2010, 25, 372-80.

The differences between P8 mice and R1 mice (control mice) were statistically analyzed by comparing sleep/wake behavior and circadian rhythm of the vehicle-treated animals of each strain, while the effect of administration of a compound of Formula (I) on sleep/wake behavior and circadian rhythm was statistically analyzed for each strain as the difference between sleep/wake behavior and circadian rhythm on the vehicle-administration day and sleep/wake behavior and circadian rhythm on a drug-administration day. Statistical analysis of wakefulness time, non-REM sleep time, REM sleep time and latency, and sleep latency was performed with a linear mixed model which specified animal as random effect, and day, strain, treatment and the interaction between strain and treatment as fixed effects with Kenward-Roger as denominator degrees of freedom using SAS software. For estimation of wakefulness phase and its covariance, a linear mixed model was used which assumed heterogeneous variance of strain and treatment combination with Kenward-Roger as denominator and degrees of freedom using SAS software.

Figure 1A:
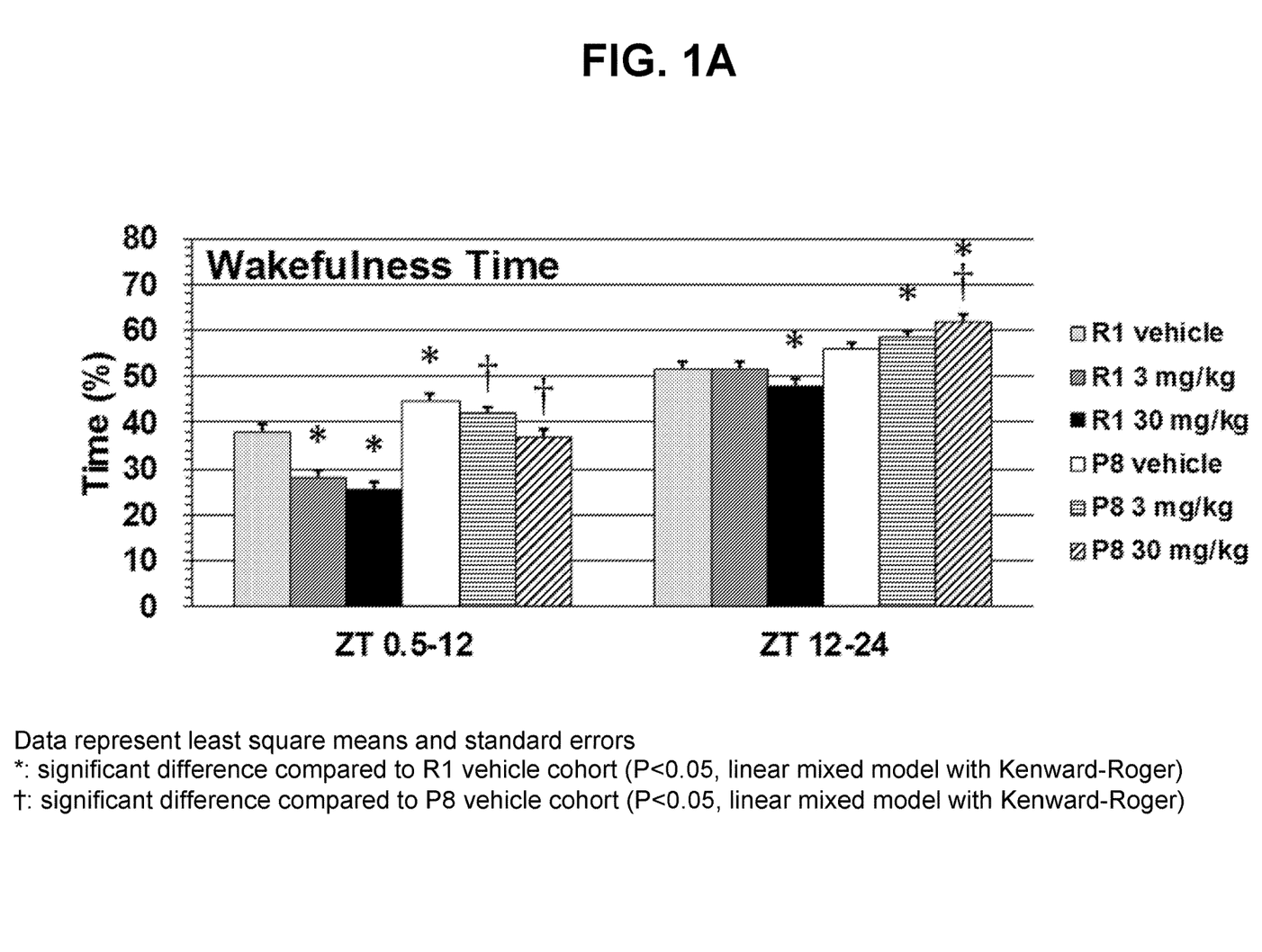
FIGS. 1A-1C show the distribution for each of the three vigilance states: wakefulness (FIG. 1A), non-REM sleep (FIG. 1B), and REM sleep (FIG. 1C) among the light (Zeitgeber (ZT) 0.5-12) and the dark (ZT 12-24) times of the circadian day, and the influence of administration of a compound of Formula (I).
Figure 1B:
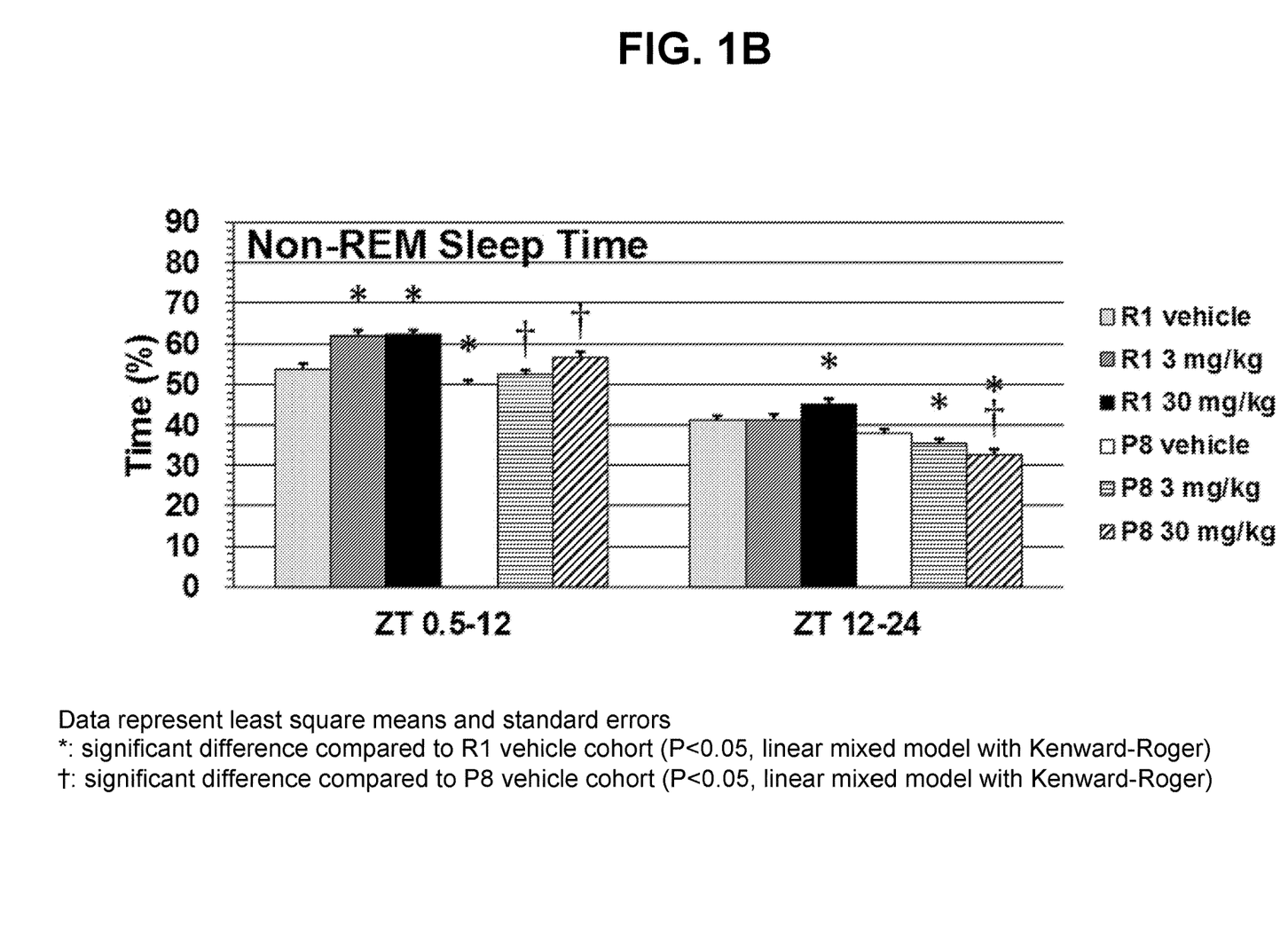
Figure 1C:
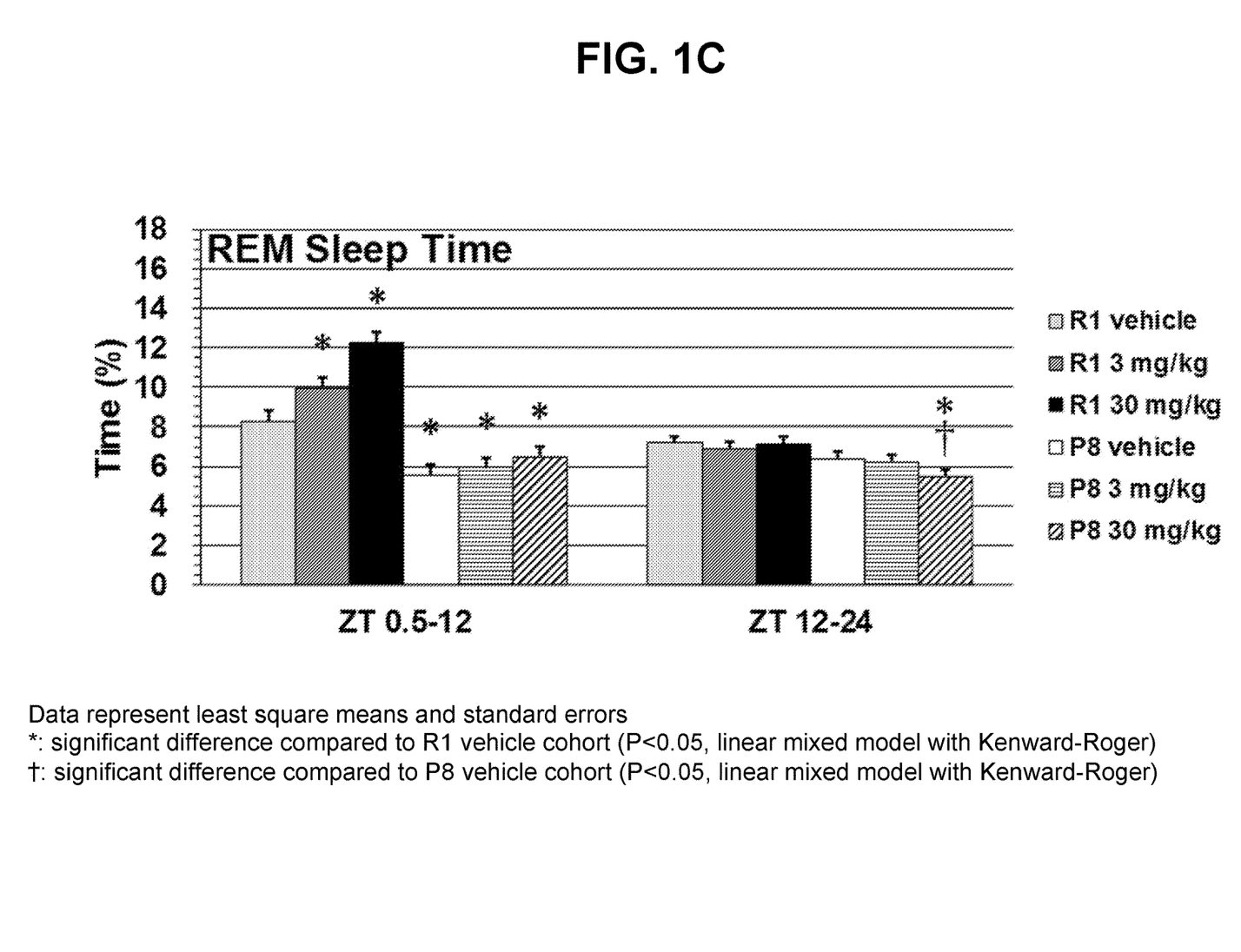

As shown in FIGS. 1A-1C, vehicle-treated P8 mice show more wakefulness, less non-REM sleep, and less REM sleep than vehicle-treated R1 mice during light time, a feature which resembles nighttime sleep disturbances in patients with Alzheimer's disease and/or related disorders. When administered at the beginning of light time, a compound of Formula (I) reduces, in a dose-dependent manner, wakefulness and increases non-REM sleep in both strains of mice, with the amounts of wake and non-REM sleep in treated P8 mice normalized to the level of vehicle-treated R1 mice. Similarly, a dose-dependent increase in the amount of REM sleep in both strains in the light time is observed.

Figure 2:
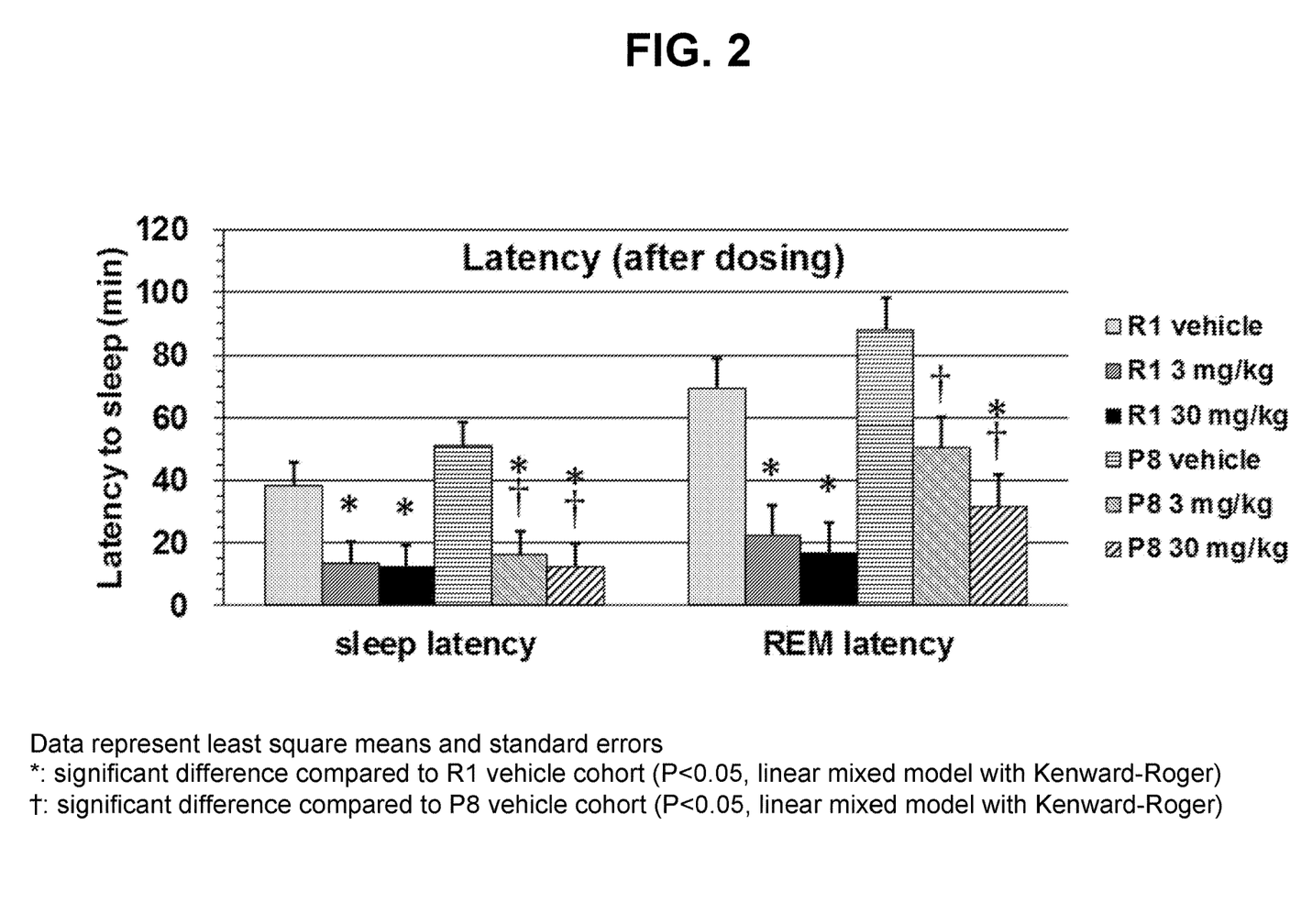
FIG. 2 shows sleep and REM sleep latency after administration of vehicle or a compound of Formula (I).

During the dark time (ZT12-24) of the circadian day, previous light time administration of a compound of Formula (I) at the 30 mg/kg dose to R1 mice led to a decrease of wakefulness and increase of non-REM sleep as shown in FIGS. 1A and 1B, respectively, while treatment with the 3 mg/kg appears to have no effect on each of the vigilance states. In contrast, administration of a compound of Formula (I) led to a dose-dependent increase in wakefulness, and decreases in non-REM sleep and REM sleep in P8 mice, as shown in FIGS. 1A, 1B, and 1C, respectively. As shown in FIG. 2, administration of a compound of Formula (I) leads to a dose-dependent reduction of sleep and REM sleep latencies in both strains of mice.

As shown in Table 2, the wake circadian phase of vehicle-treated P8 mice is significantly advanced compared to vehicle-treated R1 mice. Administration of a compound of Formula (I) during ZT 0-0.5 resulted in a dose-dependent and significant delay (right-shift) of the wake phase in P8 mice, resulting in a correction to the level of vehicle-treated R1 mice.

TABLE 2

Wake circadian phase.

| Strain | Treatment | Phase (ZT) | Covariance of Phase |
|---|---|---|---|
| R1 | vehicle | 14.45 ± 0.84 | 4.76 |
| | 3 mg/kg | 15.65 ± 0.87 | 5.18 |

TABLE 2-continued

Wake circadian phase.

| Strain | Treatment | Phase (ZT) | Covariance of Phase |
|---|---|---|---|
|  | 30 mg/kg | 17.02 ± 0.35$^a$ | 0.05 |
| P8 | vehicle | 10.31 ± 2.04 | 32.22 |
|  | 3 mg/kg | 14.00 ± 0.56 | 1.32 |
|  | 30 mg/kg | 15.41 ± 0.64$^b$ | 2.11 |

Data represent least square means and standard errors
ZT: Zeitgeber time in hours (lights on is ZT 0.0, lights off is ZT 12.0)
$^a$significant difference compared to R1 vehicle cohort (P < 0.05, linear mixed model with Kenward-Roger)
$^b$significant difference compared to P8 vehicle cohort (P < 0.05, linear mixed model with Kenward-Roger)

As indicated by the covariance, the phase variability in P8 mice is also higher than in R1 mice. When the compound of Formula (I) was administered during ZT0-0.5, a dose-dependent significant delay (right-shift) of the wake phase in P8 and R1 mice was observed, in addition to a reduction in phase covariance and phase variability.

Example 3. Treatment of Subjects with ISWRD

Subjects, both male and female with ages ranging from 60 to 90 years old, having mild or moderate Alzheimer's Disease-Dementia, and who complain of disrupted sleep or multiple awakenings at night along with frequent periods of falling asleep during the day may be screened to be eligible for treatment. The study enrollment is approximately 125 subjects and is divided into two major phases: Prerandomization and Randomization phases, where the Prerandomization phase is further divided into a Screening and a Baseline Period, and the Randomization phase is further divided into a Treatment Period and a Follow-up Period.

Prerandomization Phase

Screening Period

During an initial visit, a clinician will verify that a subject has been diagnosed with Alzheimer's Disease-Dementia and will ensure that the subject has Irregular Sleep-Wake Rhythm Disorder. This is accomplished by the subject's participation in a medical, psychiatric, and sleep history assessment, and mini-mental state examination ("MMSE") in addition to assessment of the subject's electrocardiogram, clinical laboratory tests, vital signs, height and weight.

If a subject is determined to be eligible for the study, the subject is provided with an actigraph to wear for the duration of the study. Additionally, a nocturnal sleep period will be determined, which is defined as the desired eight-hour period of time for the subject to spend in bed. The subject's caregiver is provided with a sleep log which tracks the subject's sleep time (start and end times) as well as the approximate times when the actigraph was removed from and subsequently replaced on the subject's wrist.

The subject wears the actigraph, and the subject's caregiver continues to maintain the sleep log during the Screening Period. The Screening Period consists of a period of at least 14 days (but less than 42 days) and concludes when the subject and caregiver return to the clinic to provide the clinician with the actigraph and sleep log data, in addition to adverse events and concomitant medication use.

Baseline Period

At the start of the Baseline Period, assuming that the actigraphy data confirm the diagnosis of ISWRD, the caregiver meets with the clinician and completes the Sleep Disorders Inventory ("SDI"), Neuropsychiatric Inventory-10 item version ("NPI-10"), and the Euro-QOL version 5 dimensions, 5 levels ("EQ-5D-5L"), in addition to the baseline assessment for the Clinician's Global Impression of Change-Irregular Sleep-Wake Rhythm Disorder Clinical Assessment Scale ("CGIC-ISWRD Scale") on behalf of the subject and completes the EQ-5D-5L, Zarit Burden Inventory ("ZBI-short"), and the Pittsburgh Sleep Quality Index ("PSQI") on behalf of her/himself. The subject will also complete the Alzheimer's Disease Assessment Scale-Cognitive Subscale ("ADAS-cog") and the EQ-5D-5L.

Randomization Phase

Treatment Period

Once the Baseline Period concludes, the subject begins the Treatment Period which lasts for four weeks. The subject is randomized and receives study drug of either a composition of Example 1, comprising a compound of Formula (I), or pharmaceutically acceptable salts and solvates thereof, in a dose amount of 2.5 mg, 5 mg, 10 mg, or 15 mg, or the subject is administered placebo. The study drug is provided to the caregiver and the caregiver administers the study drug to the subject within five minutes of when the subject intends to fall asleep. Subjects are requested to try to remain in bed for at least seven hours each night and to maintain the subject's sleep time as determined during the Screening Period.

At the two-week mark of the Treatment Period, the subject and caregiver return to meet with the clinician to provide actigraphic and sleep log data. The subject's vital signs are also assessed, along with reporting adverse events, concomitant medication use, and treatment compliance.

At the four-week mark of the Treatment Period, administration of study drug ceases and the subject and caregiver meet with the clinician to provide actigraphic and sleep log data. Additionally, the subject undergoes clinical laboratory tests, a blood sample for PK analysis is obtained, electrocardiogram analysis, measurement of vital signs and weight, and reporting of adverse events, concomitant medications, and treatment compliance. The caregiver completes the SDI, NPI-10, and the EQ-5D-5L on behalf of the subject and the EQ-5D-5L, ZBI-short, and PSQI on behalf of her/himself. The caregiver also provides information on the CGIC-ISWRD scale on behalf of the subject. The subject is administered the ADAS-cog, MMSE, EQ-5D-5L, eC-SSRS, and the CGIC-ISWRD Scale.

Follow-Up Period

At the cessation of study drug administration, the subject continues to wear the actigraph and the caregiver continues to maintain the sleep log for between 14 and 18 days. During that time, the subject and caregiver meet with the clinician to provide actigraphic and sleep log data. Additionally, the subject undergoes clinical laboratory tests, electrocardiogram analysis, measurement of vital signs and weight, analysis of the site of actigraph application, and reporting of adverse events and concomitant medications. This meeting concludes the subject's and caregiver's participation in the study.

Study Endpoints

Endpoints in this study are to determine the dose response of the change from baseline of sleep efficiency and wake efficiency during the last four weeks of treatment, compared with placebo, as measured using actigraphy.

Prophetic Example 1. Treatment of Subjects with ISWRD

Subjects experiencing irregular sleep-wake cycles and/or decreased alertness for more than three months may be screened to be eligible for treatment. Prior to treatment, subjects may be monitored for two weeks using actigraphy techniques.

The study may comprise approximately 125 subjects, both male and female, with ages ranging from about 65 to about 90 years old, having ISWRD. Subjects may be administered a formulation, as described below, or a placebo.

A formulation as described herein, for example, such as the composition of Example 1, comprising a compound of Formula (I), or pharmaceutically acceptable salts and solvates thereof, in a dose such as, for example, 2.5 mg, 5 mg, 10 mg, or 15 mg may be administered to subjects, for example, at night, just before bedtime. The formulation may be administered according to a dosing regimen, such as, for example, once per day each day for four weeks, or for further example, or every second day, for one week, two weeks, three weeks, four weeks, or indefinitely.

During treatment, subjects could be monitored regularly using techniques commonly known in the art, for example, actigraphy. Other subject features may be monitored before, during and/or after treatment such as postural stability and cognitive and memory performance, for example, at wake time. Subjects may also or alternatively be monitored using polysomnography, actigraphy, caregiver journals and questionnaires, and/or computerized cognitive test batteries.

An endpoint of the study may be to observe the dose response of the change from baseline of sleep efficiency and wake efficiency during the last seven nights of treatment, compared with placebo, as measured using actigraphy.

Prophetic Example 2. Treatment of Subjects with Alzheimer's Disease Suffering from Sleep-Wake Fragmentation Subjects experiencing irregular sleep-wake cycles and/or decreased alertness for more than three months may be screened on the basis of disease state (e.g., mild to moderate Alzheimer's disease) to be eligible for treatment. Prior to treatment, subjects may be monitored for two weeks using actigraphy techniques.

The study may comprise approximately 125 subjects, both male and female, with ages ranging from about 65 to about 90 years old, having irregular sleep-wake rhythm disorder and mild to moderate Alzheimer's Disease. Subjects may be administered a formulation, as described below, or a placebo.

A formulation as described herein, for example, such as the composition of Example 1, comprising a compound of Formula (I), or pharmaceutically acceptable salts and solvates thereof, in a dose such as, for example, 2.5 mg, 5 mg, 10 mg, or 15 mg may be administered to subjects, for example, at night, just before bedtime. The formulation may be administered according to a dosing regimen, such as, for example, once per day each day for four weeks, or for further example, or every second day, for one week, two weeks, three weeks, four weeks, or indefinitely.

During treatment, subjects could be monitored regularly using techniques commonly known in the art, for example, actigraphy. Other subject features may be monitored before, during and/or after treatment. Subjects may also or alternatively be monitored using polysomnography, actigraphy, caregiver journals and questionnaires, and/or computerized cognitive test batteries.

An endpoint of the study may be to observe the dose response of the change from baseline of sleep efficiency and wake efficiency during the last seven nights of treatment, compared with placebo, as measured using actigraphy.

What is claimed:

1. A method of treating irregular sleep-wake rhythm disorder in a subject comprising administering to a subject in need thereof an effective amount of at least one compound chosen from lemborexant, pharmaceutically acceptable salts thereof and solvates of any of the foregoing.

2. A method of treating at least one circadian rhythm sleep disorder in a subject with dementia due to Alzheimer's disease and/or related disorders comprising administering to a subject in need thereof an effective amount of at least one compound chosen from lemborexant, pharmaceutically acceptable salts thereof and solvates of any of the foregoing.

3. A method of treating at least one circadian rhythm sleep disorder in a subject with mild cognitive impairment due to Alzheimer's disease comprising administering to a subject in need thereof an effective amount of at least one compound chosen from lemborexant, pharmaceutically acceptable salts thereof, and solvates of any of the foregoing.

4. The method according to claim 1, wherein the subject has mild cognitive impairment due to Alzheimer's disease.

5. The method according to claim 1, wherein the irregular sleep-wake rhythm disorder is due to traumatic brain injury.

6. The method according to claim 1, wherein the irregular sleep-wake rhythm disorder is due to at least one neurodevelopmental disorder.

7. The method according to claim 1, wherein the irregular sleep-wake rhythm disorder is due to dementia due to Alzheimer's disease and/or related disorders.

8. The method according to claim 1, wherein the irregular sleep-wake rhythm disorder is due to dementia due to Alzheimer's disease.

9. The method according to claim 1, wherein the subject suffers from at least one other circadian rhythm sleep disorder in addition to irregular sleep-wake rhythm disorder.

10. The method according to claim 9, wherein the at least one other circadian rhythm sleep disorder is chosen from sleep disruption and circadian rhythm sleep disorder.

11. The method according to claim 1, wherein administration of the at least one compound chosen from lemborexant, pharmaceutically acceptable salts thereof, and solvates of any of the foregoing, consolidates sleep during the nighttime hours.

12. The method according to claim 1, wherein administration of the at least one compound chosen from lemborexant, pharmaceutically acceptable salts thereof, and solvates of any of the foregoing, consolidates wakefulness during the daytime hours.

13. The method according to claim 1, wherein the subject experiences an increase in sleep efficiency.

14. The method according to claim 1, wherein the subject experiences a decrease in daytime sleepiness and/or daytime napping.

15. The method according to claim 1, wherein the subject experiences an increase in daytime alertness.

16. The method according to claim 1, wherein the administration of the at least one compound chosen lemborexant, pharmaceutically acceptable salts thereof, and solvates of any of the foregoing, results in a stabilization of one or more circadian rhythms.

17. The method according to claim 1, wherein the administration of the at least one compound chosen from lemborexant, pharmaceutically acceptable salts thereof, and solvates of any of the foregoing, results in an improvement of one or more circadian rhythms.

18. The method according to claim 1, wherein the administration of lemborexant, pharmaceutically acceptable salts thereof, and solvates of any of the foregoing, results in an improvement of continuity of nocturnal sleep.

19. The method according to claim 1, wherein the administration of the at least one compound chosen from lemborexant, pharmaceutically acceptable salts thereof, and solvates of any of the foregoing, results in an improvement of behaviors and cognitive difficulties associated with irregular sleep-wake rhythm disorder.

* * * * *